(12) United States Patent
Clement et al.

(10) Patent No.: US 8,921,421 B2
(45) Date of Patent: Dec. 30, 2014

(54) INHIBITORS OF DIMETHYLARGININE DIMETHYLAMINOHYDROLASE

(75) Inventors: Bernd Clement, Kiel (DE); Jürke Kotthaus, Kiel (DE); Dennis Schade, Kiel (DE)

(73) Assignee: Christian-Albrechts-Universitaet Zu Kiel, Kiel (DE)

( * ) Notice: Subject to any disclaimer, the term of this patent is extended or adjusted under 35 U.S.C. 154(b) by 642 days.

(21) Appl. No.: 13/133,799

(22) PCT Filed: Dec. 8, 2009

(86) PCT No.: PCT/DE2009/001724
§ 371 (c)(1),
(2), (4) Date: Aug. 23, 2011

(87) PCT Pub. No.: WO2010/066239
PCT Pub. Date: Jun. 17, 2010

(65) Prior Publication Data
US 2011/0294878 A1    Dec. 1, 2011

(30) Foreign Application Priority Data

Dec. 10, 2008 (DE) .................. 10 2008 061 247

(51) Int. Cl.
| | | |
|---|---|---|
| *A61K 31/22* | (2006.01) | |
| *A01N 37/12* | (2006.01) | |
| *A01N 37/44* | (2006.01) | |
| *A61K 31/155* | (2006.01) | |
| *A61K 31/17* | (2006.01) | |
| *C07C 257/14* | (2006.01) | |
| *C07C 279/12* | (2006.01) | |

(52) U.S. Cl.
CPC ............. *A61K 31/155* (2013.01); *A61K 31/17* (2013.01); *C07C 257/14* (2013.01); *C07C 279/12* (2013.01)
USPC ............ 514/549; 514/550; 514/551; 514/552

(58) Field of Classification Search
CPC .. A61K 31/155; C07C 279/04; C07C 279/06; C07C 279/08; C07C 279/10; C07C 279/12; C07C 279/14
USPC .................. 514/549, 550, 551, 552
See application file for complete search history.

(56) References Cited

U.S. PATENT DOCUMENTS

| | | | | |
|---|---|---|---|---|
| 4,315,009 A | * | 2/1982 | Jones et al. | ............. 514/236.2 |
| 5,786,383 A | | 7/1998 | Clement | |
| 5,830,917 A | | 11/1998 | Moore et al. | |

FOREIGN PATENT DOCUMENTS

| | | |
|---|---|---|
| DE | 4321444 | 1/1995 |
| EP | 330 629 | 2/1989 |
| WO | WO 93/04048 | 3/1993 |
| WO | WO 97/32844 | 8/1997 |
| WO | WO 2006/051314 | 5/2006 |
| WO | WO 2008/009264 | 1/2008 |

OTHER PUBLICATIONS

Robertson et al. "*Inhibition of Bovine Brain Nitric Oxide Synthase by α-Amino and α-Carboxyl Derivatives, of $N^G$-Allyl-$_L$-arginine*", Bioorganic Chemistry, No. 23, pp. 144-151, 1995.
Kotthaus et al., "*$N^δ$-Methylated $_L$-arginine Derivatives and their Effects on the Nitric Oxide Generating System*", Bioorganic Medicinal Chemistry, No. 16, pp. 2305-2312, 2008.
Kotthaus et al., "*Structure-Activity Relationship of Novel and Known Inhibitors of Human Dimetizylarginine Dimethylaminohydrolase-1: Alkenyl-amidines as New Leads*", Bioorganic and Medicinal Chemistry, No. 16, pp. 10205-10209, 2008.
Rossiter et al., "*Selective Substrate-Based Inhibitors of Mammalian Dimethylarginine Dimethylaminohydrolase*", Journal of Medicinal Chemistry, vol. 48, No. 13, pp. 4670-4678, 2005.
Leiper et al, "*Disruption of Methylarginine Metabolism impairs Vascular Homeostasis*", Nature Medicine, vol. 13, No. 2, pp. 198-203, 2007.
Knipp et al., "*Colorimetric 96-Well Microtiter Plate Assay for the Determination of Enzymatically Formed Citrulline*", Analytical Biochemistry, No. 286, pp. 257-264, 2000.
Tassoni et al., "*Novel Substituted Aminoalkylguanidines as Potential Antihyperglycemic and Food Intake-Reducing Agents*", Journal of Medicinal Chemistry, No. S1, pp. 3073-3076, 2008.
Christen et al., "*Gesättigate offenkettige Kohlenwasserstoffe*", Grundlagen der organischen Chemie, pp. 38-39, 2012.

\* cited by examiner

*Primary Examiner* — San-Ming Hui
(74) *Attorney, Agent, or Firm* — Diederiks & Whitelaw, PLC

(57) ABSTRACT

The invention relates to an inhibitor of dimethylarginine dimethylaminohydrolase (DDAH) of general structural formula (I), wherein B is a branched or unbranched, substituted or non-substituted, saturated or unsaturated hydrocarbon chain having a chain length of 1 to 6 and/or a substituted or non-substituted aromatic system having a ring size of 3 to 6; $R^1$ is selected from the group of structures (i-vii), wherein $R^2$, $R^3$ and $R^4$ are selected from the group consisting of hydrogen, an alkyl or aryl radical, $R^5$ and $R^6$ are selected from the group consisting of hydrogen, a hydrocarbon chain having a chain length of 1 to 8 and an aryl radical, $R^7$, $R^8$, $R^9$ and $R^{10}$ are selected from the group consisting of hydrogen, and alkyl or aryl radical; W is oxygen (O) or nitrogen (N); and X is a methylene group ($CH_2$) or a secondary amino group (NH); Y is a branched or unbranched, substituted or non-substituted, saturated or unsaturated hydrocarbon chain having a chain length of 1 to 6 and/or a substituted or non-substituted aromatic system having a ring size of 3 to 6; Z is hydrogen (H) or a methoxyl group; and the radical (B) carrying the amino group has no carboxyl group.

7 Claims, No Drawings

INHIBITORS OF DIMETHYLARGININE DIMETHYLAMINOHYDROLASE

CROSS-REFERENCE TO RELATED APPLICATIONS

This application represents a National Stage application of PCT/DE2009/001724 entitled. "Inhibitors of Dimethylarginine Dimethylaminohydrolase" filed Dec. 8, 2009, pending.

BACKGROUND OF THE INVENTION

1. Field of the Invention

The present invention relates to new inhibitors of dimethylarginine dimethylaminohydrolase (DDAH).

2. Discussion of the Prior Art

The DDAH catalyses the physiological decomposition of $N^\omega$-monomethyl-L-arginine (NMMA) and $N^\omega,N^\omega$-dimethyl-L-arginine (ADMA) to form L-citrulline and mono- or dimethylamine. These $N^\omega$-methylated L-arginines are formed by methylation of protein-bound arginine radicals by the isoenzymes of the protein-arginine-methyltransferases (PRMTs). The protein decomposition releases these two substances and they circulate in physiological concentrations of 0.4 to 1.0 μM in the blood. In pathological conditions however, the values can increase markedly (up to 10 μM).

Both ADMA and NMMA are potent inhibitors of all three isoenzymes of the nitrogen monoxide synthase (NOS) that catalyse the release of nitrogen monoxide (NO) from L-arginine. NO regulates as a potent vasodilatator the vascular tonus, protects against atherosclerotic events and is involved as neurotransmitter in a multiplicity of functions such as memory performance or the formation of pain. In addition, NO has an important role in the unspecified immune defence.

On account of this variety of functions of NO, a balanced regulation of the NO biosynthesis is vital. A reduced NO biosynthesis can lead to cardiovascular diseases such as hypertension, atherosclerosis or coronary heart disease and erectile dysfunction.

On top of this, a multiplicity of pathological states is associated with an overproduction of NO so that an inhibition of NO biosynthesis can be exploited for treating these diseases. Examples, for such pathophysiological states are the disease patterns of the septic shock, the stroke, neurodegenerative diseases, chronic inflammations, rheumatoid arthritis, migraine, inflammatory pain (nociception), diabetes mellitus and meningitis.

Despite the fact that many attempts have been made over the previous years to exploit a direct inhibition of the NO synthase pharmaceutically for treating these disease patterns, none of the tested compounds has been approved as a medicinal product.

The inhibition of DDAH represents a new approach for the indirect inhibition of the isoenzymes of the NO synthase. The inhibition of DDAH leads to a rise in the blood level of $N^\omega$-methylated L-arginines and thus to an indirect inhibition of the activity of NOS. In the meantime, several studies confirmed an influence of the NO biosynthesis as a result of a modulation of the DDAH activity. It was thus found in animal models that an inhibition of DDAH leads to a rise in the ADMA blood level and the vascular tonus (Rossiter, Smith et al. 2005; Leiper, Nandi et al. 2007). On top of this, selective DDAH-1 inhibitors are candidates for treating chronic pain and the septic shock (Leiper, Nandi et al. 2007). Inhibition of DDAH can be assumed as a further indication possibility in the treatment of neurodegenerative diseases such as for Morbus Alzheimer, since in the case of this disease pattern, both a reduced ADMA blood level and an increased DDAH activity could be detected.

Over the previous years, a co-expression of DDAH-1 with nNOS and a co-localisation of DDAH-2 with eNOS and partly with iNOS could be detected. As a result, a selective inhibition of DDAH-1 can possibly be used for the selective reduction of the activity of nNOS. In the meantime, use of selective DDAH-1 inhibitors was successfully tested in vivo for treating chronic pain and the septic shock. Involvement of DDAH-1 in tumour growth and the angiogenesis was also detected. Tumour tissue with increased DDAH-1 expression proliferated much faster than other tumour tissue.

On the other hand, inhibition of DDAH-2 makes little sense, since a reduced endothelial NO release represents a risk factor for cardiovascular complications.

Previously known inhibitors for the human DDAH-1 are the L-arginine derivatives. The at present most potent representative of this group is $N^\omega$-(2-methoxyethyl)-L-arginine (L-257, $IC_{50}$ 22 μM, murine DDAH), a guanidine (Rossiter, Smith et al. 2005). On top of this, the $N^\delta$-(1-iminoalk(en)yl-L-ornithines are a very potent inhibitor class with vinyl-L-NIO as the at present most potent known inhibitor of DDAH-1 (Kotthaus, Schade et al. 2008).

It is known to increase the oral bioavailability of the guanidines and amidines by means of prodrug principles. Here, a very successful principle are the N-hydroxyamidines (amidoximes) and N-hydroxyguanidines [Clement, B. DE4321444 and PCT/DE2007/001216].

The inhibitors known so far for human DDAH-1 exhibit bad pharmacokinetic properties due to their amino acid structure since they exist as zwitterions in the case of a physiological pH. The amino function is protonated and thus positively charged, while the carboxyl function is deprotonated and is thus negatively charged. Charged substances are resorbed from the gastrointestinal tract only to a small extent, since they cannot penetrate the lipophile membranes of the gastrointestinal tract by diffusion. The passive diffusion however represents the preferred absorption mechanism of a medicinal product after oral administration. It is thus very unlikely that effective substance levels in the blood are reached after the oral administration of charged compounds. In addition, there is also the possibility of the intake via specific transport systems like the amino acid transporter, however the extent of resorption by means of this mechanism has to be assessed to be much reduced. For this reason, removing charges from a molecule is of eminent importance for the development of medicinal products that are to exhibit an oral bioavailability.

SUMMARY OF THE INVENTION

It is thus the object of the invention to provide new specific inhibitors of the human DDAH-1 that exhibit improved pharmacokinetic properties.

More specifically, the invention is directed to an inhibitor of dimethylarginine dimethylaminohydrolase (DDAH) of general structural formula

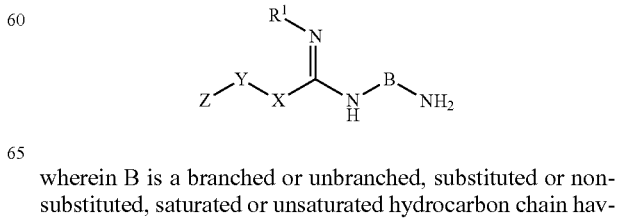

wherein B is a branched or unbranched, substituted or non-substituted, saturated or unsaturated hydrocarbon chain having a chain length of 1 to 6 and/or a substituted or non-substituted aromatic system having a ring size of 3 to 6, $R^1$ is selected from the group of structures (i-vii):

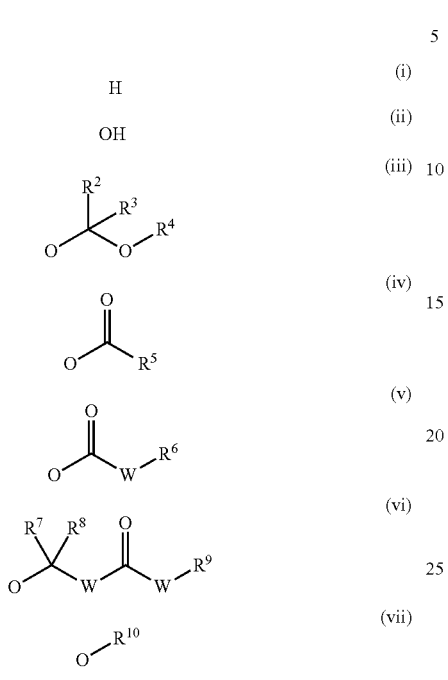

wherein $R^2$, $R^3$, $R^4$ are selected from the group consisting of hydrogen, an alkyl or aryl radical, $R^5$, $R^6$ are selected from the group consisting of hydrogen, a hydrocarbon chain having a chain length of 1 to 8 and an aryl radical, $R^7$, $R^8$, $R^9$, $R^{10}$ are selected from the group consisting of hydrogen, an alkyl or aryl radical, W is oxygen (O) or nitrogen (N); and X is a methylene group ($CH_2$) or a secondary amino group (NH), Y is a branched or unbranched, substituted or non-substituted, saturated or unsaturated hydrocarbon chain having a chain length of 1 to 6 and/or a substituted or non-substituted aromatic system having a ring size of 3 to 6, Z is hydrogen (H) or a methoxyl group and the radical (B) carrying the amino group has no carboxyl group, as well as various uses thereof.

DETAILED DESCRIPTION OF THE INVENTION

Within the framework of the invention, new inhibitors of the human DDAH-1 were synthesised and tested for their effectiveness. The inventive inhibitors are represented by the following general structural formula:

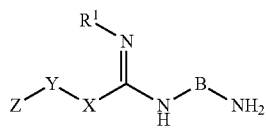

wherein
B is a branched or unbranched, substituted or non-substituted, saturated or unsaturated hydrocarbon chain having a chain length of 1 to 6 and/or a substituted or non-substituted aromatic system having a ring size of 3 to 6;

R1 corresponds to the structures (i-vii):

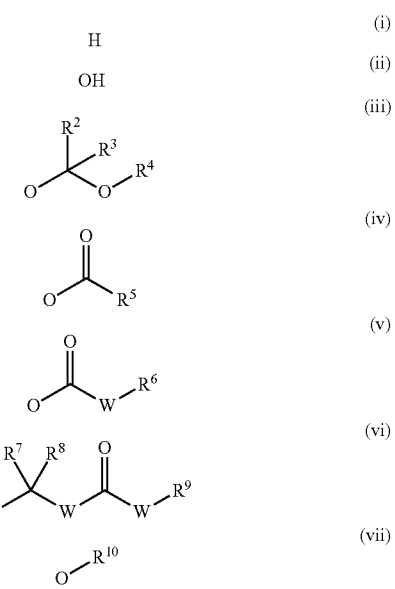

wherein
R2-4 can correspond to hydrogen, alkyl or aryl radicals or can be designed such that in terms of their structure they correspond to a monosaccharide (derivative), R5-6 can correspond to hydrogen, a hydrocarbon chain having a chain length of 1 to 8 or an aryl radical, R7-10 can correspond to hydrogen, alkyl or aryl radicals and W corresponds to an oxygen or a nitrogen atom,
X carbon (C) or nitrogen (N),
Y is a branched or unbranched, substituted or non-substituted, saturated or unsaturated hydrocarbon chain having a chain length of 1 to 6 and/or a substituted or non-substituted aromatic system having a ring size of 3 to 6,
Z is hydrogen or a methoxyl group,
and
the radical (B) carrying the amino group has no carboxylic group,
possible substituents for Y being selectable from halogen (fluorine, chlorine, bromine or iodine), oxygen, sulphur, alkoxy, acyloxy, amino; hydroxyl, carbonyl, mercapto, carboxy, benzyloxy, phenyl, benzyl, cyano, nitro, thioalcoxy, carboxyaldehyde, carbalcoxy and carboxamide, or a functionality that can be suitable blocked with a protected group and possible substituents for B being selectable from halogen (fluorine, chlorine, bromine and iodine), sulphur, alkoxy, amino, hydroxyl, carbonyl, mercapto, benzyloxy, phenyl, benzyl, cyano, nitro, thioalcoxy or a functionality that can be suitably blocked with a protective group;
and the salts of these compounds.
It is to be understood that if X is carbon (C) or nitrogen (N), a methylene group (—CH2-) or a secondary amino group (—NH—) can be present instead of X.
A comparison with the composition L-257 already known as inhibitor of the human DDAH shows that for the first time also compounds without α-carboxyl function as they exists in amino acids likewise effect a potent inhibition of the hDDAH-1. Not restricting the generality of the teachings, Table 1 shows an overview of the inhibition values on the hDDAH-1. The data that are illustrated for the inhibition for 1 mM are MV±SD of at least four separate incubations that were in each case measured twice. The IC50 and Ki values were determined at least twice. n.d.=not determined.

TABLE 1

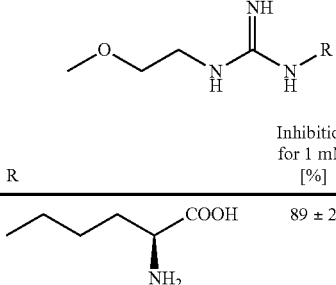

| Substance | R | Inhibition for 1 mM [%] | IC$_{50}$ [µM] | K$_i$ [µM] |
|---|---|---|---|---|
| L-257 | 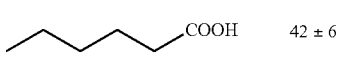 | 89 ± 2 | 29 ± 7 | 13 ± 2 |
| CbMEG | COOH | 42 ± 6 | n.d. | n.d. |
| 3 | NH$_2$ | 80 ± 5 | 70 ± 16 | 18 ± 6 |

The recognition that the α-carboxyl function is not essential is remarkable since the crystal structure of DDAH-1 underlines the importance of the α-carboxyl function of amino acids since it forms three ionic interactions to the active centre of DDAH-1. The inventive exemplary embodiment 3 shows a potent inhibition of DDAH-1 and on account of the loss of the α-carboxyl function in comparison to L-257 it exhibits improved pharmacokinetic properties so that the absorption probability from the gastrointestinal tract is increased.

The recognition that the α-carboxyl function is not essential was transferred to N$^δ$-(1-iminoalk(en)yl)-L-ornithines (Table 2). The exemplary embodiment 5, too, shows an inhibition of the DDAH-1 so that a development of inhibitors without α-carboxyl function is likewise possible on the amidine basis.

TABLE 2

| Substance | | Inhibition for 1 mM [%] |
|---|---|---|
| 5 | 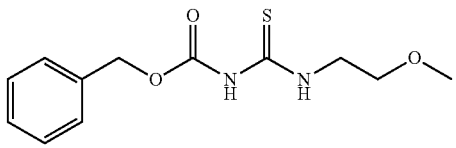 [SMILES: COCCNC(=S)NC(=O)OCc1ccccc1] | 40 ± 6 |

The data illustrated for the inhibition for 1 mM are MV±SD of at least four separate incubations that have each been measured twice.

These findings surprisingly show for the first time that the development of potent inhibitors without α-carboxyl function that are thus not associated with the pharmacokinetic disadvantages of the amino acids is possible.

To improve the oral bioavailability of the inventive inhibitors of the human DDAH-1, prodrug principles that are known can be used for amidines and guanidines, in particular N-hydroxyamidines (amidoximes) and N-hydroxyguanidines corresponding to [Clement, B. Methoden zur Behandlung und Prophylaxe der *Pneomocystis carinii*. Pneumonie (PCP) und anderen Erkrankungen sowie Verbindungen und Formulierungen zum. Gebrauch bei besagten Methoden (Methods for treating and prophylaxis of *Pneomocystis carinii* pneumonia (PCP) and other diseases and compounds and formulations for use with said methods). P. 432444.4, 1993].

The inventive inhibitors of the human DDAH-1 can generally be used for treating diseases and pathophysiological states that are due to an overproduction of NO. The indications that can be used are the septic shock, chronic or non-chronic pain, stroke, chronic or non-chronic inflammations, rheumatoid arthritis, migraine, asthma, ischemia/reperfusion traumata of the heart or the brain, hypotony or neurodegenerative diseases. Lower ADMA blood levels were found in particular in Alzheimer patients than in healthy control groups, so that treatment using DDAH inhibitors seems promising here. In addition, DDAH inhibitors can also be used for treating tumour diseases, sepsis or peritonitis.

MATERIALS AND METHODS

Exemplary Embodiment A

N-(4-aminobutyl)-N'-(2-methoxyethyl)guanidine
N-benzyloxycarbonyl-N'-(2-methoxyethyl)-thiourea
(1)

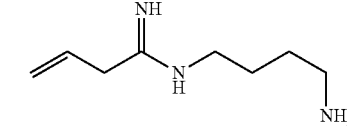

General Specification Pursuant to Linton, Carr et al. 2000:

7.0 mmol 2-methoxyethylamine were dissolved in 250 mL of dry dichloromethane. The solution was cooled to 0° C. and added drop-Wise to 14 mL of a 0.5 M solution (in dichloromethane)benzyloxycarbonylisothiocyanate (7.0 mmol) over a period of 30 minutes. The reaction mixture was stirred for two hours, the solution warming up to room temperature in the process. The mixture was then evaporated on the rotary evaporator to approximately one third of the original volume in vacuum and washed in each case using 25 mL of 1% HCl, water and saturated NaCl solution. The organic phase is dried over Na$_2$SO$_4$ and removed using the rotary evaporator. At this point, the thiourea 1 is already mostly >96% pure (TLC) and is purified further by crystallisation. The raw product that is obtained after using the rotary evaporator then crystallises spontaneously while producing great heat. It is then ground with little cold cyclohexane; filtered and washed using cold cyclohexane in small portions and dried.

Yield: 1.76 g white crystals (94%)

TLC: R$_f$=0.30 (cyclohexane/ethylacetate, 4:1)

Melting point: 88.5° C.

$^1$H-NMR (CDCl$_3$):

δ/ppm=3.39 (s, 3H, O—CH$_3$), 3.60 (t, $^3$J=5.2 Hz, 2H, O—CH$_2$), 3.86 (q, $^3$J=5:2 Hz, 2H, N—CH$_2$), 5.19 (s, 2H, CH$_2$-Cbz), 7.32-7.61 (m, 5H, ArH), 8.11 (br s, 1H, NH), 9.84 (br s, 1H, NH).

$^{13}$C-NMR (CDCl$_3$):

δ/ppm=46.2 (N—CH$_2$), 59.6 (O—CH$_3$), 68.8 (O—CH$_2$), 70.4 (O—CH$_2$), 129.0, 129.4, 129.5 (ArCH), 135.2 (ArC), 153.0 (CO), 179.9 (C=S).

MS (ESI):

m/z=269 [M+H]$^+$, 225 [M–CO$_2$+H]$^+$, 91 [C$_7$H$_7$]$^+$.

C$_{12}$H$_{16}$N$_3$O$_2$S (268.33)

Calculated C, 53.71; H, 6.01; N, 10.44.

Found C, 53.93; H, 6.19; N, 10.61.

N-benzyloxycarbonyl-N'-[4-(t-butyloxycarbonyl)aminobutyl]-N''-(2-methoxyethyl)guanidine (2)

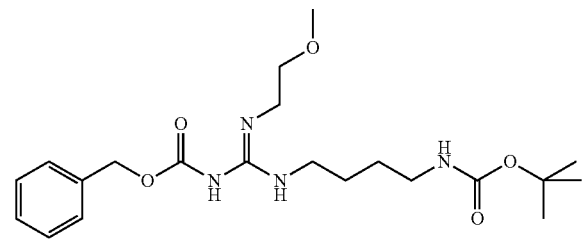 [SMILES: COCC/N=C(\NCCCCNC(=O)OC(C)(C)C)NC(=O)OCc1ccccc1]

General Specification Pursuant to Linton, Carr et al. 2000:

0.5 mmol of the thiourea 1 are dissolved in 5 mL dry dichloromethane and 261 μL DIPEA (1.5 mmol) and 1.5 mmol N-boc-1,4-diaminobutane are added. The solution is brought to 0° C. for about 30 minutes and 287 mg EDCI (1.5 mmol) are added. To the extent that nothing else is specified, the mixture is stirred over night at room temperature. The solution is diluted with approximately 10 mL of dichloromethane and washed in each case with 5 mL 1% HCl, water and saturated NaCl solution. The organic phase was dried over Na$_2$SO$_4$ and evaporated on the rotary evaporator. It is mostly oils that result that are further purified using flash chromatography over silica gel. The eluting agents that are used and the yields that are achieved are specified in connection with the respective substances.

Dichloromethane/methanol (95:5) is used as eluting agents.

Yield: 198 mg of a colourless oil (94%)

TLC: R$_f$=0.41 (dichloromethane/methanol, 96:4; reagents A and C)

$^1$H-NMR (CDCl$_3$):

δ/ppm=1.36 (s, 9H, C(CH$_3$)$_3$), 1.41-4.57 (m, 4H, N—CH$_2$—CH—CH$_2$), 3.06, 3.19°(2×m, 2H, N—CH$_2$), 3.30 (s, 3H, O—CH$_3$), 3.31-3.44 (m, 4H, N—CH$_2$—CH$_2$—O), 4.56 (br s, 1H, NH), 5.04 (s, 2H, CH$_2$-Cbz), 7.24-7.36 (m, 3H, ArH), 7.39-7.43 (m, 2H, ArH), 9.19 (br s, 1H, NH).

$^{13}$C-NMR (CDCl$_3$):

δ/ppm=27.1, 28.2 (N—CH$_2$—CH$_2$—CH$_2$), 29.1 (C(CH$_3$)$_3$), 40.7, 41.4 (3×N—CH$_2$), 59.6 (O—CH$_3$), 67.2 (O—CH$_2$, CH$_2$—Cbz), 80.0 (C(CH$_3$)$_3$), 128.2, 128.6, 128.9 (ArCH), 138.5 (ArC), 156.7 (C=N), 164.8 (CO).

MS (ESI):

m/z=423 [M+H]$^+$.

N-(4-aminobutyl)-N'-(2-methoxyethyl)guanidine bis(trifluoracetate)(3)

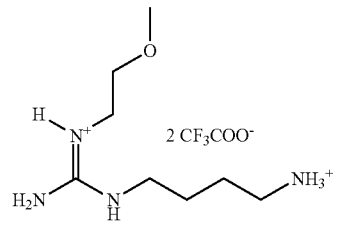

The protected guanidine 2 (0.5 mmol) is stirred over night with 10 mL of TFA and 3 mL of thioanisole at room temperature. The major part of TFA is then distilled off in vacuum and 5 mL of water and 15 mL of diethyl ether are added. The organic phase is extracted twice with 5 mL of water and the combined aqueous phases are then finally washed using 5 mL of diethyl ether. The aqueous phase is concentrated in vacuum and purified chromatographically. The raw product is purified by means of flash chromatography across an RP-18 column (eluting agent: 0.1% TFA$_{(aq)}$). The ninhydrin-positive fractions are combined and concentrated under vacuum.

Yield: 234 mg of a clear oil (99%)

TLC: R$_f$=0.22 (i-propanol/water/glacial acetic acid, 8:2+ 0.5; reagent A)

$^1$H-NMR (DMSO-d$_6$):

δ/ppm=1.54 (m, 4H, N—CH$_2$—CH$_2$—CH$_2$), 2.80 (m, 2H; N—CH$_2$), 3.14 (m, 2H, N—CH$_2$), 3.27 (s, 3H, O—CH$_3$), 3.32, 3.42 (2×t, 4H, N—CH$_2$—CH$_2$—O), 7.47 (br s, 2H, NH$_2$), 7.61 (br t, 1H, NH), 7.71 (br t, 1H, NH), 7.87 (br s, 3H, NH$_3^+$).

$^{13}$C-NMR (DMSO-d$_6$):

δ/ppm=24.1 (CH$_2$—CH$_2$—NH$_3^+$), 25.4 (CH$_2$—CH$_2$—CH$_2$—NH$_3^+$), 38.3 (N—CH$_2$), 40.3 (N—CH$_2$), 40.7 (N—CH$_2$), 58.0 (O—CH$_3$), 70.0 (O—CH$_2$), 155.9 (C=N).

MS (ESI):

m/z=1.89 [M+H]$^+$.

C$_8$H$_{16}$N$_4$O$_5$.2,5 CF$_3$COOH (473.33)

Calculated C, 32.99; H, 4.79; N, 11.84.

Found C, 32.86; H, 4.80; N, 11.50.

Exemplary Embodiment B

N-(4'-aminobutyl)but-3-enamidine N-[4'-(t-butyloxycarbonyl)-aminobutyl]but-3-enamidine hydrochloride (4)

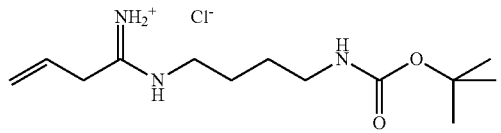 [SMILES: [Cl-] ; C=CCC(=[NH2+])NCCCCNC(=O)OC(C)(C)C]

188 mg of N-(t-butyloxycarbonyl)-1,4-diaminobutane (1 mmol) and 407 mg but-3-enimidic acid methyl ester hydrochloride (3 mmol) are dissolved in 10 mL of water at 0° C. 2.5 M of NaOH are added to this solution until a pH of approximately 10 is achieved and the solution is then stirred for two hours at 0° C. and for one hour at room temperature. The reaction mixture is brought to pH 7 using diluted HCl and stirred over night at room temperature. The mixture is concentrated at approximately 30° C. using the rotary evaporator and worked up using column chromatography over silica gel, an ethylacetate/methanol gradient being used (step-wise: 20-40% methanol).

Yield: 250 mg of a white hazy oil (86%)
TLC: $R_f$=0.1.7 (ethylacetate/methanol, 8:2; reagent A)
$^1$H-NMR (DMSO-$d_6$):
δ/ppm=1.36 (s, 9H, C(CH$_3$)$_3$), 1.39-1.54 (m, 4H, 2',3'-CH$_2$), 2.91 (m, 2H, 4'-CH$_2$), 3.18-129 (m, 4H, 2,1'-CH$_2$), 5.20 (dd, $^3J_{cis}$=10.0 Hz, $^2J$=1.3 Hz, 1H, CH=C$\underline{H}_2$), 5.30 (dd, $^3J_{trans}$=17.0 Hz, $^2J$=1.5 Hz, 1H, CH=C$\underline{H}_2$), 5.91 (ddt, $^3J$=6.8, 10.0, 17.0 Hz, 1H, C$\underline{H}$=CH$_2$), 6.81, 8.87, 9.40, 9.98 (4×br s, 1H, NH).
$^{13}$C-NMR (DMSO-$d_6$):
δ/ppm=24.6, 26.6 (2',3'-CH$_2$), 28.2 (C($\underline{C}$H$_3$)$_3$), 36.0 (2-CH$_2$), 39.2, 41.5 (1',4'-CH$_2$), 77.3 ($\underline{C}$(CH$_3$)$_3$), 119.7 (CH=$\underline{C}$H$_2$), 130.9 ($\underline{C}$H=CH$_2$), 155.5 (CO), 164.7 (C=N).
MS (ESI):
m/z=278 [M+Na]$^+$, 256 [M+H], 200 [M-C$_2$H$_8$+H]$^+$.

N-(4'-aminobutyl)but-3-enamidine bis(trifluoracetate)(5)

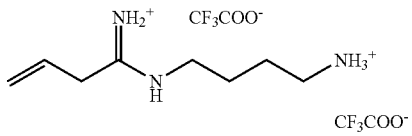

220 mg of the boc-protected amidine 44 (0.75 mmol) are stirred in 5 mL of TFA/dichloromethane (1:1) for 30 minutes at room temperature. The mixture is concentrated under vacuum, 5 mL of water are added to it and it is then washed twice using diethyl ether. The solution is concentrated by rotary evaporator down to approximately 1-2 mL and worked up further using flash chromatography across an RP-18 column. 0.1% of TFA in Aqua bidest. is used as the eluting agent.

Yield: 285 mg of a colourless oil (99%)
TLC: $R_f$=0.35 (i-propanol/water/glacial acetic acid, 8:2+0.5; reagent A)
$^1$H-NMR (DMSO-$d_6$):
δ/ppm=1.57 (m, 4H, 2',3'-CH$_2$), 2.81 (m, 2H, 4'-C$_2$), 3.17-3.26 (m, 4H, 2,1'-CH$_2$), 5.23-5.31 (m, 2H, CH=C$\underline{H}_2$), 5.87 (ddt, $^3J$=17.0, 10.0, 6.7 Hz, 1H, C$\underline{H}$=CH$_2$), 7.86 (br s, 3H, NH$_3$$^+$), 8.74, 9.16, 9.57 (3×br s, 1H, NH).
$^{13}$C-NMR (DMSO-$d_6$):
δ/ppm=24.1, 24.2 (2',3'-C$_2$), 36.5 (2-CH$_2$), 38.2, 41.2 (1', 4'-CH$_2$), 120.0 (CH=$\underline{C}$H$_2$), 130.4 ($\underline{C}$H=CH$_2$), 165.1 (C=N).
MS (ESI):
m/z=156 [M+H]$^+$, 139 [M-NH$_3$+H]$^+$.
C$_8$H$_{17}$N$_3$.2.5 CF$_3$COOH.0.5 H$_2$O (449.31)
Calculated C, 34.75; H, 4.60; N, 9.35.
Found C, 34.92; H, 4.75; N, 9.10.

Construction of the Expression Plasmid for hDDAH-1
cDNA from human DDAH-1 was procured from RZPD (Berlin, Germany) and amplified by PCR. Sense primer: 5'-AA GGATCCATGGCCGGGCTCGGCCAC-3" (with an interface for BamHI (underlined)); anti-sense: 5'-GG AAGCTTGCAGCTCAGGAGTCT-3' (with an interface for HindIII (underlined)).

The following Cycler programme was used for PCR amplification:

|   |   | T [° C.] | Time [s] |   |
|---|---|---|---|---|
| 1. | Denaturation | 94 | 180 |   |
| 2. | Denaturation | 94 | 30 | } 28 cycles |
|   | Annealing | 45 | 45 |   |
|   | Extension | 72 | 180 |   |
| 3. | Extension | 72 | 900 |   |
| 3. | Hold | 4 | ∞ |   |

The PCR product was ligated into the expression vector pQE-30 (Qiagen, Hilden, Germany) using the interfaces BamHI and HindIII.

Expression and Purification of his-Tagged Human DDAH-1

For the enzyme expression, the expression plasmid was transformed into BL-21 cells and an overnight broth was prepared in kanamycin and ampicillin-containing LB medium at 37° C. On the day of the expression, one liter of LB medium was inoculated using 50 ml of the overnight broth and incubated at 30° C. until an OD$_{600}$ of 0.6 was achieved. The expression was induced using isopropyl-β-thiogalacto-pyranoside (IPTG) in a concentration of 100 μM. The expression time was between 4 and 6 h at a temperature of 30° C. After the termination of the expression, the cells were centrifuged off (4,500 g, 4° C., 10 min). The pellet was suspended for immediate use in 26 ml of cell-lysis buffer (20 mM of K$_2$HPO$_4$, 150 mM of NaCl, 2 mM of 2-mercaptoethanol, 1 mM of phenylmethylsulfonylfluoride and 1 mM of benzamidine) and the cells were lysed using a French press at 19,000 psi (4° C.). This process was repeated twice. The coarse cell fragments were then centrifuged off (4,500 g, 4° C. 10 min) and the supernatant was freed from the finer cell fragments using ultracentrifugation at 33,000 g for 45 minutes at 4° C.

300 μl of Ni$^{2+}$ NTA matrix was added to the supernatant. At 4° C., the protein was bound to the matrix over 1.5 h with slight shaking. The protein was then washed using imidazol-containing solutions (50 mM of potassium phosphate buffer pH 7.0, 300 mM of NaCl, 0.5 mM of 2-mercaptoethanol, 1 mM of EDTA, 1 mM of benzamidine, 1 mM of phenylmethylsulfonylfluoride and 10% glycerol) and/or the protein was eluted according to the following method:

Washing with 2 ml of wash solution
Washing with 2 ml of wash solution (+10 mM of imidazol)
Washing with 1 ml of wash solution (+20 mM of imidazol)
Elution with 1 ml of wash solution (+100 nM of imidazol)

In Vitro hDDAH-1 Assay (HPLC)
This assay was used to determine the inhibiting effect of the inhibitors in a concentration of 1 mM. A standard incubation mixture consisted of 75 μl of 50 mM potassium phosphate buffer pH 7.4 and contained NMMA in a concentration of 200 μM. The inhibitors were used in final concentrations of 1 mM. By adding 2 μg of hDDAH-1, the reaction was started and the samples were incubated for 30 minutes at 37° C. in, a shaking water bath. The reaction was then stopped by adding 75 μl of acetonitrile, the samples were shaken for 5' minutes and centrifuged (12,000 g, 5 min). The supernatant was added to the HPLC.

In addition, three incubations without added inhibitor were carried out in each case and worked up as specified above. The L-citrulline concentration detected in the samples was set at 100% and the amount of L-citrulline formed in the samples with added inhibitor was referred to this value.

Determination of the $IC_{50}$ Value (Plate-Reader Assay)

The samples for the plate-reader assay were incubated directly on a 96-well microtiter plate. An incubation mixture consisted of 150 μl of 50 mM potassium phosphate buffer pH 7.4 with NMMA in a final concentration of 300 μM. The inhibitor was added in five different concentrations and the reaction was started by adding 4 μg of recombinant hDDAH-1. In addition, two mixtures without added inhibitor were incubated. The plate was closed with a lid and incubated for 30 minutes on a plate incubator (shaker DTS-4, LTF-Labortechnik GmbH, Wasserburg, Germany) at 37° C. The reactions were stopped using 200 μl of the Colder reagent and the citrulline that had formed was derivatised (see derivatisation for plate-reader assay). The $IC_{50}$ value was then calculated by means of SigmaPlot 8.0 (SPSS Chicago, USA).

Determination of the $K_i$ Value (Plate-Reader Assay)

The $K_i$ value was determined as described for the $IC_{50}$ value, with the difference that five different NMMA concentrations (50, 100, 300, 750 and 1250 μM) were used. The incubations were carried out such that each NMMA concentration was in each case incubated twice with each of the five inhibitor concentrations. On top of this, incubations using the different NMMA concentrations were carried out without added inhibitor.

For each inhibitor concentration, using SigmaPlot 8.0 (SPSS Inc., Chicago, USA) the respective apparent $K_m$ value and $V_{max}$ were determined. Via secondary plotting of the inhibitor concentrations versus $K_m/V_{max}$ the $K_i$ value was determined by extrapolation of the least-squares lines onto the abscissa.

Derivatisation for Plate-Reader Assay

For derivatising citrulline, two reagent solutions were prepared:

| Solution A | Solution B | | |
|---|---|---|---|
| 80 mM diacetylmonoxime | | 200 ml | 85% $H_3PO_4$ |
| 2 mM thiosemicarbazide | | 330 ml | 96% $H_2SO_4$ |
| | | 750 mg | $NH_4Fe(SO_4)_2 \times 12 H_2O$ |
| | ad | 1000 ml | Aqua bidest. |

The derivatisation reagent (Colder reagent) was prepared immediately prior, to derivatisation by mixing one part of solution A with three parts of solution B and was stored protected against direct irradiation by the sun.

Derivatisation was carried out on particularly heat-stable 96-well microtiter plates. 200 μl of the Colder reagent was added to the samples (150 μl) and to prevent evaporation, the plate was closed with a heat-stable adhesive film (Nunc, Wiesbaden, Germany). Colour formation then took place in the drying oven at 95° C. for 15-20 minutes. Before photometric measurements were taken, there was a wait until the plate had reached room temperature and then the colour intensity at 540.5 nm (Carry 50 microplate reader, Varian, Darmstadt, Germany) was measured. Measurement took place during 20 minutes since the reaction product is not stable (Knipp and Vasak 2000).

HPLC Method

For analysing the samples of the in vitro hDDAH-1 assay (HPLC), o-PA pre-column derivatisation was used with subsequent fluorescence detection of the amino acids.

HPLC plant: Waters Autosampler 717plus, Waters 600 Controller, Waters 600 Pump, Waters Fluorescence Detector 470 and EZChrom Elite Client/Server Measurement and evaluation software (version 2.8.3)

Stationary phase: NovaPak RP-18 column 4 μm (4×150 mm, VDS Optilab) pre-column: Phenomenex C18 (4×3.0 mm)

Temperature: 30° C.

| Mobile phase: | Eluting agent A: | 10 mM of potassium | 86% |
| | | phosphate buffer pH 4.65 | |
| | | acetonitrile | 8% |
| | | methanol | 6% |
| | Eluting agent B: | acetonitrile | 40% |
| | | methanol | 30% |
| | | aqua bidest. | 30% |
| Flow rate: | 1 ml/min | | |

Gradient profile:

| Time [min] | Eluting agent A [%] | Eluting agent B [%] |
|---|---|---|
| 0 | 100 | — |
| 2 | 100 | — |
| 3.5 | 90 | 10 |
| 12 | 90 | 10 |
| 16 | 25 | 75 |
| 25 | 25 | 75 |
| 28 | 100 | — |
| 35 | 100 | — |

Detection: Fluorescence: $\lambda_{ex}$: 338 nm; 425 nm.

Injection volume: 10 μl

Derivat. reagent: 50 mg o-PA dissolved in 1 ml of methanol
+9 ml 0.2 M of potassium borate buffer pH 9.4
+53 μl 2-mercaptoethanol Derivatisation: The auto sampler was programmed such that 10 μl of the sample were mixed with 14 μl of the derivatisation reagent and could react for 3 minutes at room, temperature prior to injection.

Retention times:

L-citrulline 12.2±0.3 min

NMMA 15.8±0.4 min

Methylamine 23.4±0.1 min

The invention claimed is:

1. An inhibitor of dimethylarginine dimethylaminohydrolase (DDAH) of general structural formula

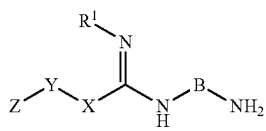

wherein
B is a branched or unbranched, non-substituted, saturated or unsaturated hydrocarbon chain having a chain length of 1 to 6, R¹ is selected from the group of structures (i-iii):

(i) H
(ii) OH
(iii) 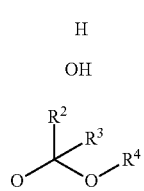

wherein
R², R³, R⁴ are an alkyl radical; and
X is a secondary amino group (NH),
Y is a branched or unbranched, substituted, saturated or unsaturated hydrocarbon chain having a chain length of 1 to 6,
Z is a methoxyl group
and
the radical (B) carrying the amino group has no carboxyl group.

2. The inhibitor according to claim 1, characterised in that R¹ having the structure (iii) is a monosaccharide or a monosaccharide derivative.

3. The inhibitor according to claim 1, characterised in that B and/or Y are polyunsaturated.

4. The inhibitor according to claim 1, characterised in that Y has substituents selected from the group consisting of a halogen, in particular fluorine, chlorine, bromine or iodine, oxygen, sulphur, an alkoxy, acyloxy, amino, hydroxyl, carbonyl, mercapto, carboxy, benzyloxy, phenyl, benzyl, cyano, nitro, thioalcoxy, carboxyaldehyde, carbalcoxy and carboxamide group.

5. A method comprising a step of administering an inhibitor of dimethylarginine dimethylaminohydrolase (DDAH), said inhibitor having the general structural formula

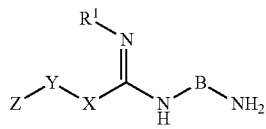

wherein
B is a branched or unbranched, substituted or non-substituted, saturated or unsaturated hydrocarbon chain having a chain length of 1 to 6,
R¹ is selected from the group of structures (i-iii):

(i) H
(ii) OH
(iii) 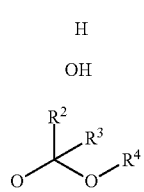

wherein
R², R³, R⁴ are an alkyl radical; and
X is a secondary amino group (NH),
Y is a branched or unbranched, substituted or non-substituted hydrocarbon chain having a chain length of 1 to 6,
Z is a methoxyl group
and
the radical (B) carrying the amino group has no carboxyl group for preparing a medicinal product for treating a disease whose pathology is accompanied by an oversupply of endogenous nitric oxides ($NO_x$).

6. A method comprising a step of administering an inhibitor of dimethylarginine dimethylaminohydrolase (DDAH), said inhibitor having the general structural formula

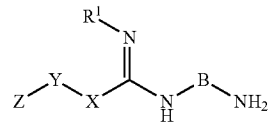

wherein
B is a branched or unbranched, substituted or non-substituted, saturated or unsaturated hydrocarbon chain having a chain length of 1 to 6,
R¹ is selected from the group of structures (i-iii):

(i) H
(ii) OH
(iii) 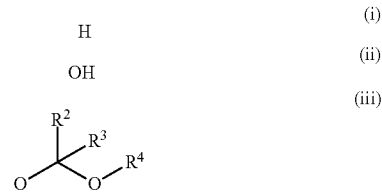

wherein
R², R³, R⁴ are an alkyl radical; and
X is a secondary amino group (NH),
Y is a branched or unbranched, substituted or non-substituted hydrocarbon chain having a chain length of 1 to 6,
Z is a methoxyl group
and
the radical (B) carrying the amino group has no carboxyl group for treating the ischemia/reperfusion traumata of the heart or the brain, hypotony, (chronic) inflammation, neurodegenerative disorders, tumour diseases, peritonitis, asthma, migraine, pain, sepsis or septic shock.

7. A method comprising a step of administering an inhibitor of dimethylarginine dimethylaminohydrolase (DDAH), said inhibitor having the general structural formula

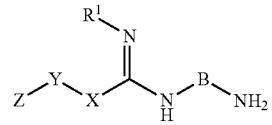

wherein
B is a branched or unbranched, substituted or non-substituted, saturated or unsaturated hydrocarbon chain having a chain length of 1 to 6, $R^1$ is selected from the group of structures (i-iii):

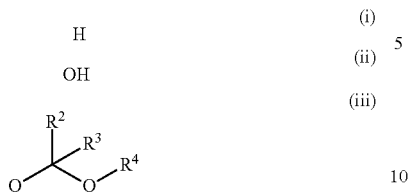

(i) H
(ii) OH
(iii) [structure with $R^2$, $R^3$, $R^4$]

wherein
$R^2$, $R^3$, $R^4$ are an alkyl radical; and
X is a secondary amino group (NH),
Y is a branched or unbranched, substituted or non-substituted, saturated or unsaturated hydrocarbon chain having a chain length of 1 to 6,
Z is a methoxyl group
and
the radical (B) carrying the amino group has no carboxyl group for preparing a medicinal product for prophylaxis of pain.

* * * * *